United States Patent
Jung et al.

(10) Patent No.: US 11,168,180 B2
(45) Date of Patent: Nov. 9, 2021

(54) POLYETHYLENE GLYCOL DERIVATIVE AND PREPARATION METHOD THEREOF

(71) Applicant: Hanmi Fine Chemical Co., Ltd., Siheung-Si (KR)

(72) Inventors: Yong Gyu Jung, Gunpo-Si (KR); Bo Sung Kwon, Suwon-Si (KR); Seung Hwan Kwak, Siheung-Si (KR); Eun Rang Park, Bucheon-Si (KR); Kyung Do Kim, Siheung-Si (KR); Hyun Sik Yun, Siheung-Si (KR); Hyung Woo Lee, Seongnam (KR); Young Bum Cho, Anyang-Si (KR)

(73) Assignee: Hanmi Fine Chemical Co., Ltd.

(*) Notice: Subject to any disclaimer, the term of this patent is extended or adjusted under 35 U.S.C. 154(b) by 0 days.

(21) Appl. No.: 16/648,443

(22) PCT Filed: Nov. 6, 2018

(86) PCT No.: PCT/KR2018/013381
§ 371 (c)(1),
(2) Date: Mar. 18, 2020

(87) PCT Pub. No.: WO2019/088800
PCT Pub. Date: May 9, 2019

(65) Prior Publication Data
US 2020/0231749 A1    Jul. 23, 2020

(30) Foreign Application Priority Data
Nov. 6, 2017  (KR) .................. 10-2017-0146940

(51) Int. Cl.
| | | |
|---|---|---|
| C07C 41/30 | (2006.01) | |
| C08G 65/333 | (2006.01) | |
| C07C 43/13 | (2006.01) | |
| C07C 213/02 | (2006.01) | |
| C07C 217/76 | (2006.01) | |
| C07C 303/04 | (2006.01) | |
| C07C 303/28 | (2006.01) | |
| C07C 309/68 | (2006.01) | |
| C07C 309/75 | (2006.01) | |

(52) U.S. Cl.
CPC ........ *C08G 65/33306* (2013.01); *C07C 41/30* (2013.01); *C07C 43/135* (2013.01); *C07C 213/02* (2013.01); *C07C 217/76* (2013.01); *C07C 303/04* (2013.01); *C07C 303/28* (2013.01); *C07C 309/68* (2013.01); *C07C 309/75* (2013.01)

(58) Field of Classification Search
None
See application file for complete search history.

(56) References Cited

U.S. PATENT DOCUMENTS

| | | |
|---|---|---|
| 2005/0238617 A1 | 10/2005 | Li et al. |
| 2012/0004423 A1 | 1/2012 | Engell |
| 2018/0186931 A1 | 7/2018 | Kinbara et al. |
| 2019/0071379 A1 | 3/2019 | Kim et al. |

FOREIGN PATENT DOCUMENTS

| | | |
|---|---|---|
| JP | 2011084632 A | 4/2011 |
| KR | 101245071 B1 | 3/2013 |
| KR | 20170104409 A | 9/2017 |
| WO | 2017002853 A1 | 1/2017 |

OTHER PUBLICATIONS

LaBeaume et al. (Bioorganic & Medicinal Chemistry, 2009, (17), 6292) (Year: 2009).*
Oba, M. et al, "Cyclic RGD Peptide-Conjugated Polyplex Micelles as a Targetable Gene Delivery System Directed to Cells Possessing rvâ3 and rvâ5 Integrins" Bioconjugate Chem. published on web Jun. 27, 2007, 18, 1415-1423.
International Search Report for PCT/KR2018/013381 dated Apr. 19, 2019.

* cited by examiner

*Primary Examiner* — Sudhakar Katakam
*Assistant Examiner* — Jennifer C Sawyer
(74) *Attorney, Agent, or Firm* — Lerner, David, Littenberg, Krumholz & Mentlik, LLP

(57) ABSTRACT

The present invention relates to a polyethylene glycol derivative and a preparation method thereof. A preparation process of a polyethylene glycol derivative, according to the present invention, may provide a novel polyethylene glycol derivative which can be utilized in various ways as a drug linker, and is appropriate and effective for mass production and is advantageous in reproducible mass production of high-quality products.

4 Claims, 1 Drawing Sheet

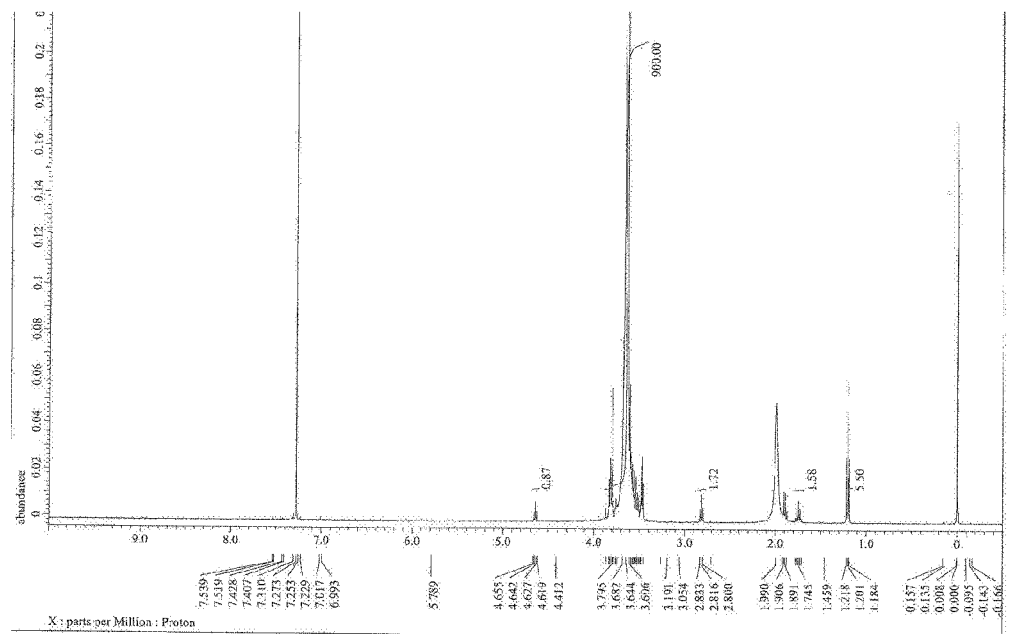

POLYETHYLENE GLYCOL DERIVATIVE AND PREPARATION METHOD THEREOF

CROSS-REFERENCE TO RELATED APPLICATIONS

The present application is a national phase entry under 35 U.S.C. § 371 of International Application No. PCT/KR2018/013381, filed Nov. 6, 2018, which claims priority from Korean Patent Application No. 10-2017-0146940, filed on Nov. 6, 2017, the disclosures of which are incorporated herein by reference in their entirety.

TECHNICAL FIELD

The present invention relates to a polyethylene glycol derivative and a preparation method thereof. More specifically, the present invention relates to a polyethylene glycol derivative substituted with functional groups at both ends and an efficient preparation method thereof.

BACKGROUND ART

Polyethylene glycol (PEG) is one of the polymers that have strong hydrophilicity and thus effectively form hydrogen bonds with water molecules. PEG has excellent solubility in various organic solvents other than water and has little toxicity, and thus can be used in various applications in the development of pharmaceuticals. For example, PEG can bind to a variety of bioactive substances, such as proteins and enzymes, and thus reduce the toxicity of drugs, increase the solubility of poorly soluble drugs, and regulate the activity and half-life in blood, thereby forming PEG-drug complexes with desired properties.

In the case of a protein drug, there is a problem that since the half-life in the blood is short when administered to the human body, the frequency of infusion is increased to maintain the efficacy, and as a result, the medication adaptability is lowered. In order to solve this problem, efforts are being made to increase the half-life of the protein drug in the blood through pegylation by which polyethylene glycol binds with the protein drug. This pegylation not only can increase the half-life of the protein drug in the blood but also reduce the antigenicity of the protein drug, so the pegylation of the protein drug is widely used in protein therapeutics.

In order to bind PEG and a protein drug, PEG derivatives in which various functional groups are introduced into the hydroxyl group (OH group) at the chain end of PEG are used. Examples of such PEG derivatives comprise PEG-aldehyde, PEG-acetaldehyde, PEG-propionaldehyde, and the like. The aldehyde groups present at the ends of these derivatives can selectively react with the amino terminus of a protein. In addition, to bind PEG with protein drug and immunoglobulin Fc, the ends of PEG derivatives may have a maleimide group, a succinimide derivative (succinimidyl propionate, hydroxy succinimidyl, succinimidyl carboxymethyl or succinimidyl carbonate), and the like.

There is a need for a more efficient method for producing a polyethylene glycol derivative used as a linker in preparing such bioactive polypeptide conjugates.

DISCLOSURE

Technical Problem

It is an object of the present invention to provide a method for producing a novel polyethylene glycol derivative.

It is another object of the present invention to provide an intermediate used in the preparation method of the novel polyethylene derivatives and a method of preparing the same.

Technical Solution

In order to achieve the above objects, the present invention provides a method for preparing the following compound of Formula 7 comprising the steps of:

(1) preparing the following compound of Formula 2 from the following compound of Formula 1 under a base;

(2) reacting the compound of Formula 2 with the following compound of Formula 2-1 under a base to produce the following compound of Formula 3;

(3) preparing the following compound of Formula 4 from the compound of Formula 3 under a base;

(4) reacting the compound of Formula 4 with the following compound of Formula 5 under a base to produce the following compound of Formula 6; and (5) debenzylating the compound of Formula 6 to produce the following compound of Formula 7.

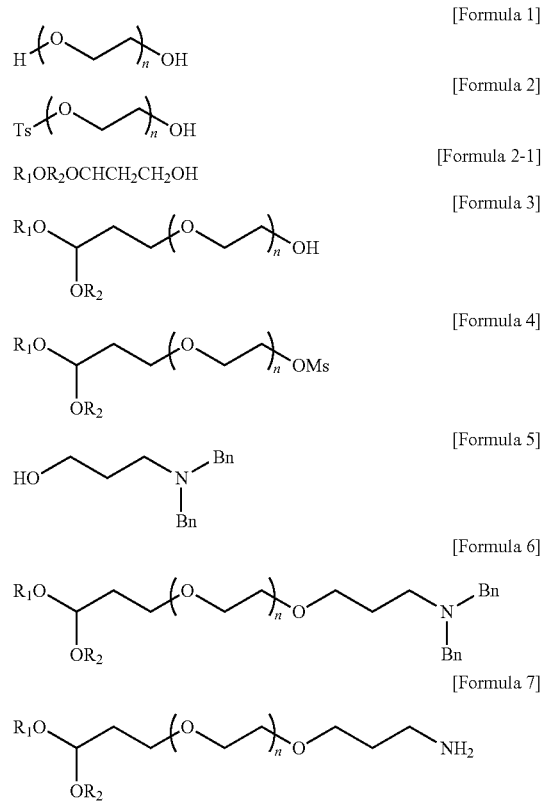

wherein Ts is toluenesulfonyl, Ms is methanesulfonyl, Bn is benzyl, $R_1$ and $R_2$ are each independently a linear or branched $C_1$–$C_9$ alkyl group, and n is an integer from 3 to 2000.

In addition, the present invention provides a compound of Formula 2 below, which is an intermediate used in the preparation method of the polyethylene derivatives.

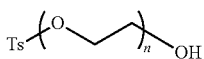
[Formula 2]

wherein Ts is toluenesulfonyl, and n is an integer from 3 to 2000.

In addition, the present invention provides a compound of Formula 8 below, which is an intermediate used in the preparation method of the polyethylene derivatives.

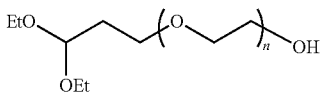
[Formula 8]

wherein Et is ethyl, and n is an integer from 3 to 2000.

In addition, the present invention provides a compound of Formula 9 below, which is an intermediate used in the preparation method of the polyethylene derivatives.

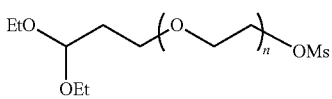
[Formula 9]

wherein Et is ethyl, Ms is methanesulfonyl, and n is an integer from 3 to 2000.

In addition, the present invention provides a compound of Formula 10 below, which is an intermediate used in the preparation method of the polyethylene derivatives.

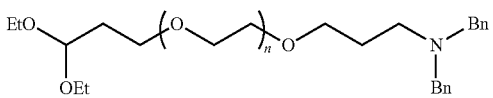
[Formula 10]

wherein Et is ethyl, Bn is benzyl, and n is an integer from 3 to 2000.

In addition, the present invention provides a compound of Formula 7 below, which is an intermediate used in the preparation method of the polyethylene derivatives.

Advantageous Effects

The preparation process of a polyethylene glycol derivative according to the present invention may provide a novel polyethylene glycol derivative which can be utilized in various ways as a drug linker, and is appropriate and effective for mass production and is advantageous in reproducible mass production of high-quality products.

DESCRIPTION OF DRAWINGS

FIG. 1 is a result of NMR analysis of Example 5-1.

BEST MODE

Hereinafter, the present invention will be described in detail.

The method for preparing the polyethylene glycol derivative of the present invention comprises the steps of:

(1) preparing the following compound of Formula 2 from the following compound of Formula 1 under a base;

(2) reacting the compound of Formula 2 with the following compound of Formula 2-1 under a base to produce the following compound of Formula 3;

(3) preparing the following compound of Formula 4 from the compound of Formula 3 under a base;

(4) reacting the compound of Formula 4 with the following compound of Formula 5 under a base to produce the following compound of Formula 6; and (5) debenzylating the compound of Formula 6 to produce the following compound of Formula 7:

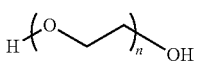
[Formula 1]

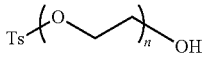
[Formula 2]

$R_1OR_2OCHCH_2CH_2OH$
[Formula 2-1]

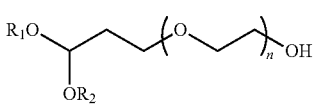
[Formula 3]

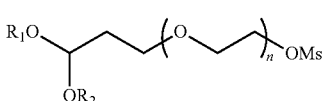
[Formula 4]

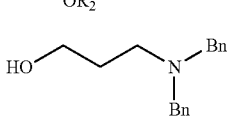
[Formula 5]

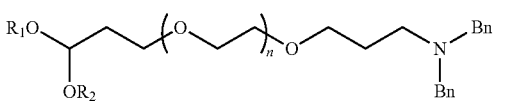
[Formula 6]

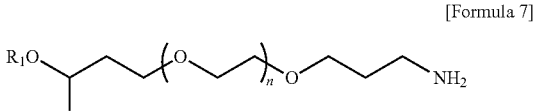
[Formula 7]

wherein Ts is toluenesulfonyl, Ms is methanesulfonyl, Bn is benzyl, $R_1$ and $R_2$ are each independently a linear or branched $C_1$–$C_9$ alkyl group, and n is an integer from 3 to 2000.

The preparation method of a polyethylene glycol derivative according to the present invention may provide a novel polyethylene glycol derivative which can be utilized in various ways as a drug linker, and is appropriate and effective for mass production and is advantageous in reproducible mass production of high-quality products.

According to one embodiment of the invention, n is directly related to the molecular weight of the polyethylene glycol derivatives to be finally prepared, and may be an integer from 3 to 2000. Also, n in the preparation method above is 7 to 1000 or 10 to 1000, specifically 50 to 500, more specifically 100 to 500, even more specifically 150 to 250, or an integer from 225±25, but is not limited to these.

According to one embodiment of the invention, $R_1$ and $R_2$ may be the same as or different from each other and specifically may be identical. $R_1$ and $R_2$ may be each independently a linear or branched $C_1$~$C_9$ alkyl group, specifically each independently methyl, ethyl, propyl, isopropyl, butyl, isobutyl, hexyl, heptyl, octyl, or nonyl, more specifically a linear or branched $C_1$~$C_4$ alkyl group, even more specifically methyl, ethyl, propyl, isopropyl, or butyl. For example, $R_1$ and $R_2$ may be ethyl.

According to one embodiment of the invention, the base may be a linear or branched $C_1$ to $C_5$ alkoxide compound or a linear or branched $C_1$ to $C_8$ amine compound. Specifically, the base may be selected from the group consisting of sodium methoxide, sodium ethoxide, sodium t-butoxide, sodium t-pentoxide (t-PeONa), potassium t-butoxide (t-BuOK), potassium t-pentoxide, trimethylamine, triethylamine (TEA), tributylamine, and mixtures thereof.

The preparation method of the present invention will be described for each step in more detail below.

Step (1) may be a step of preparing a compound of Formula 2 by toluene sulfonation of the compound of Formula 1.

Specifically, step (1) may be a step of preparing the compound of Formula 2 by reacting the compound of Formula 1 with a toluenesulfonyl halide compound.

The toluenesulfonyl halide may be toluenesulfonyl chloride, toluenesulfonyl bromide, and toluenesulfonyl iodide, and specifically may be p-toluenesulfonyl chloride, p-toluenesulfonyl bromide, and p-toluenesulfonyl iodide.

In one specific embodiment of the present invention, step (1) may be a step of preparing the following compound of Formula 2 by reacting the following compound of Formula 1 (polyethylene glycol) with p-toluenesulfonyl chloride (TsCl) under a base as shown in Reaction Scheme 1 below.

[Reaction Scheme 1]

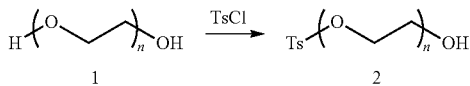

Step (1) can be applied even when n is large, and step (1) can inhibit the production of impurities such as ditosylated polyethylene glycol (ditosylated PEG) and unreacted PEG or flexible materials, and can easily purify the impurities or the flexible materials sequentially by a work-up process of the reaction using water to obtain monotosylated polyethylene glycol of Formula 2 in high yield of 90% or more.

Here, Ts and n are as described above.

In step (1), the base may be a linear or branched $C_1$ to $C_5$ alkoxide compound or a linear or branched $C_1$ to $C_8$ amine compound. Specifically, the base may be selected from the group consisting of sodium methoxide, sodium ethoxide, sodium t-butoxide, sodium t-pentoxide (t-PeONa), potassium t-butoxide (t-BuOK), potassium t-pentoxide, trimethylamine, triethylamine (TEA), tributylamine, and mixtures thereof, and more specifically triethylamine (TEA).

In step (1), the solvent may be dichloromethane (DCM), toluene, but is not limited thereto.

The reaction of step (1) can be carried out at room temperature.

In step (2), the following compound of Formula 3 is prepared by reacting compound of Formula 2 prepared in step (1) with compound of Formula 2-1 under a base, as shown in Reaction Scheme 2 below.

[Reaction Scheme 2]

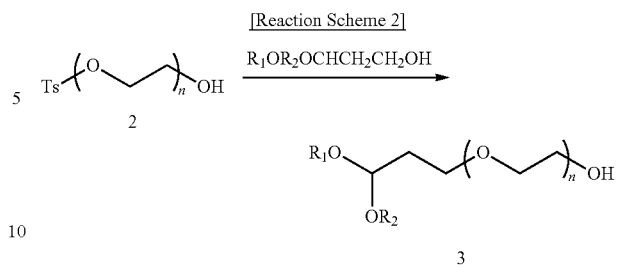

wherein Ts, n, $R_1$ and $R_2$ are as previously described.

In one specific embodiment of the invention, the compound of Formula 2-1 in step (2) is di-($C_1$-$C_5$) alkoxy propanol. For example, the alkoxy group may be a linear or branched $C_1$ to $C_5$ alkoxy, and more specifically dimethoxy-1-propanol, diethoxy-1-propanol (DEP-OH), dipropoxy-1-propanol, dibutoxy-1-propanol, diisopropoxy-1-propanol, or mixtures thereof, and even more specifically diethoxy-1-propanol.

In step (2), the base may be a linear or branched $C_1$ to $C_5$ alkoxide compound or a linear or branched $C_1$ to $C_8$ amine compound. Specifically, the base may be selected from the group consisting of sodium methoxide, sodium ethoxide, sodium t-butoxide, sodium t-pentoxide (t-PeONa), potassium t-butoxide (t-BuOK), potassium t-pentoxide, trimethylamine, triethylamine (TEA), tributylamine, and mixtures thereof, and more specifically potassium t-butoxide (t-BuOK).

In step (2), the solvent may be toluene, but is not limited thereto.

The reaction of step (2) may be carried out at 20~50° C.

Step (3) is a step of preparing a compound of Formula 4 by methane sulfonation of the compound of Formula 3 under a base.

Specifically, step (3) may be a step of preparing a compound of Formula 4 by reacting the compound of Formula 3 with a methanesulfonyl halide compound.

The methanesulfonyl halide may be methanesulfonyl chloride, methanesulfonyl bromide, and methanesulfonyl iodide.

Step (3) is a step of preparing the compound of Formula 4 by reacting the compound of Formula 3 prepared in step (2) with methanesulfonyl chloride under a base, as shown in Reaction Scheme 3 below.

[Reaction Scheme 3]

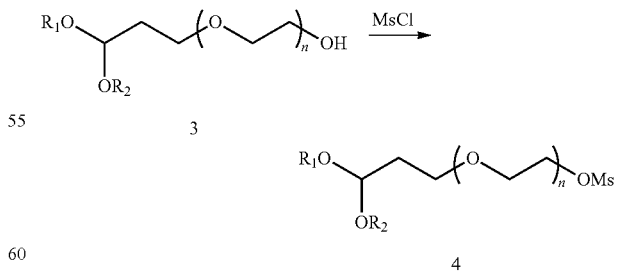

wherein Ms, n, $R_1$ and $R_2$ are as previously described.

In step (3), the base may be a linear or branched $C_1$ to $C_5$ alkoxide compound or a linear or branched $C_1$ to $C_8$ amine compound. Specifically, the base may be selected from the group consisting of sodium methoxide, sodium ethoxide, sodium t-butoxide, sodium t-pentoxide (t-PeONa), potassium t-butoxide (t-BuOK), potassium t-pentoxide, trimethylamine (TEA), triethylamine (TEA), tributylamine, and mixtures thereof, and more specifically triethylamine (TEA).

In step (3), the solvent may be, for example, dichloromethane (DCM), but is not limited thereto.

In a specific embodiment, the reaction of step (3) can be carried out, for example, at 0~25° C.

Step (4) may be a step of preparing the following compound of Formula 6 by reacting the compound of Formula 4 prepared in step (3) with the following compound of Formula 5 (dibenzylaminopropanol) under a base, as shown in Reaction Scheme 4.

[Reaction Scheme 4]

$$R_1O\diagdown\diagdown(O\diagdown)_n OMs \xrightarrow{5} $$
$$\begin{array}{c} OR_2 \\ 4 \end{array}$$

$$R_1O\diagdown\diagdown(O\diagdown)_n O\diagdown\diagdown N\diagup^{Bn}_{Bn}$$
$$\begin{array}{c} OR_2 \\ 6 \end{array}$$

wherein Ms, Bn, n, $R_1$, and $R_2$ are as previously described.

In step (4), the base may be a linear or branched $C_1$ to $C_5$ alkoxide compound or a linear or branched $C_1$ to $C_8$ amine compound. Specifically, the base may be selected from the group consisting of sodium methoxide, sodium ethoxide, sodium t-butoxide, sodium t-pentoxide (t-PeONa), potassium t-butoxide (t-BuOK), potassium t-pentoxide, trimethylamine, triethylamine (TEA), tributylamine and mixtures thereof, and more specifically potassium t-butoxide (t-BuOK) and potassium t-pentoxide.

In step (4), the solvent may be toluene, but is not limited thereto.

The reaction of step (4) may be carried out at 20~50° C.

Step (5) is a step of debenzylation of the compound of Formula 6, as shown in Reaction Scheme 5 below.

[Reaction Scheme 5]

$$R_1O\diagdown\diagdown(O\diagdown)_n O\diagdown\diagdown N\diagup^{Bn}_{Bn} \longrightarrow$$
$$\begin{array}{c} OR_2 \\ 6 \end{array}$$

$$R_1O\diagdown\diagdown(O\diagdown)_n O\diagdown\diagdown NH_2$$
$$\begin{array}{c} OR_2 \\ 7 \end{array}$$

wherein Bn, n, $R_1$ and $R_2$ are as previously described. In the present invention, the debenzylation refers to a reaction of replacing a benzyl group with hydrogen.

When the compound of Formula 7 is prepared from the compound of Formula 6 through step (5) represented by Reaction Scheme (5), the compound of Formula 7 can be produced under a mild condition with high purity and high yield, and the formation of impurities can be minimized. Also, by using the compound represented by Formula 6, the purification is easy, thereby eliminating the need for complex purification processes such as the purification of resins, and the purity of Formula 7 can be remarkably improved, thereby easily mass-producing the compound of Formula 7.

According to one embodiment of the present invention, the reaction temperature in step (5) may be 10~50° C., and typically, the compound of Formula 7 can be prepared in high yield and purity even at room temperature.

According to one embodiment of the invention, the step (5) of producing the compound of Formula 7 may be carried out in the presence of a metal catalyst. Here, the metal catalyst used for debenzylation can be used. For example, platinum oxide, palladium hydroxide, and palladium-carbon may be used as the metal catalyst, and more specifically, for example, palladium-carbon (Pd/C) may be used.

The metal catalyst may be used in an amount of 0.001 to 50 equivalents based on 1 equivalent of the compound of Formula 6, but usually 0.05 to 20 equivalents, preferably 0.1 to 5 equivalents.

According to one embodiment of the invention, step (5) may be performed in the presence of a compound represented by Formula A below.

$$N-R_aR_bR_c \quad \text{[Formula A]}$$

wherein $R_a$, $R_b$, and $R_c$ are each independently H or a linear or branched $C_1$ to $C_5$ alkyl group, and at least one of $R_a$, $R_b$, and $R_c$ is H.

The compound represented by Formula A may be ammonia, primary amine, or secondary amine, and for example, may be ammonia, methylamine, ethylamine, isopropylamine, dimethylamine, diethylamine, and the like, and specifically, may be ammonia, methylamine, and dimethylamine, but is not limited thereto.

The compound of Formula A may be added in the form of an aqueous solution containing Compound A, and specifically may be added in the form of an aqueous solution in which a concentration of the compound of Formula A is 20% (v/v) to 60% (v/v), specifically 20% (v/v) to 55% (v/v).

According to one embodiment of the invention, step (5) can be carried out in the presence of hydrogen ($H_2$).

When step (5) of the present invention is carried out in the presence of hydrogen ($H_2$), it can be carried out at a hydrogen pressure of 1 to 30 atm, but typically, compounds of Formula 7 can be prepared in high yield and purity even at atmospheric pressure.

In one embodiment of the invention, step (5) may be a step of preparing the compound of Formula 7 by reacting the compound of Formula 6 prepared in step (4) with hydrogen in the presence of a metal catalyst and the compound represented by Formula A, as shown in Reaction Scheme 5.

[Reaction Scheme 5-1]

$$R_1O\diagdown\diagdown(O\diagdown)_n O\diagdown\diagdown N\diagup^{Bn}_{Bn} \xrightarrow[H_2]{N-RaRbRc}$$
$$\begin{array}{c} OR_2 \\ 6 \end{array}$$

-continued

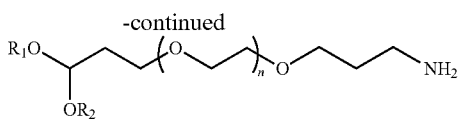

7 wherein n, $R_1$, $R_2$, $R_a$, $R_b$, and $R_c$ are as previously described.

In the present specification, the compound represented by Formula A may be ammonia, primary amine, or secondary amine, and for example, may be ammonia, methylamine, ethylamine, isopropylamine, dimethylamine, diethylamine, and the like, and specifically, may be ammonia, methylamine, and dimethylamine, but is not limited thereto.

By adding the compound represented by Formula A, the compound of Formula 7 can be synthesized in large quantity under mild reaction environment at high yield through debenzylation from the compound of Formula 6.

The compound of Formula A may be added in the form of an aqueous solution containing Compound A, and specifically may be added in the form of an aqueous solution in which a concentration of the compound of Formula A is 20% (v/v) to 60% (v/v), specifically 20% (v/v) to 55% (v/v).

In one specific embodiment of the preparation method of the present invention, when the debenzylation step is carried out by hydrogenation in the presence of the amine compound of Formula A, the compound of Formula 7 can be produced under a mild condition with high purity and high yield, and the formation of impurities can be minimized. Also, by using the compound represented by Formula 6, the purification is easy, thereby eliminating the need for complex purification processes such as the purification of resins, and the purity of Formula 7 can be remarkably improved, thereby easily mass-producing the compound of Formula 7.

In another specific embodiment of the present invention, step (5) may be a step of preparing the compound of Formula 7 by reacting the compound of Formula 6 with ammonium formate.

In step (5), the reaction solvent may be linear or branched $C_1$ to $C_5$ alcohol, water, or mixtures thereof.

In step (5), the reaction time is appropriately selected by the reaction conditions, but can usually be carried out for 1 to 48 hours.

The present invention provides a compound of Formula 2 below, which is an intermediate used in the preparation method of the polyethylene derivatives.

[Formula 2]

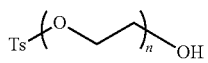

wherein Ts is toluenesulfonyl, and n is directly related to the molecular weight of the polyethylene glycol derivatives to be finally prepared, wherein n may be an integer from 3 to 2000, preferably 7 to 1000 or 10 to 1000, specifically 50 to 500, more specifically 100 to 500, even more specifically 150 to 250, or an integer from 225±25, but is not limited to these.

According to embodiments of the invention, n in the compound of Formula 2 may be 150 to 250.

The present invention provides a compound of Formula 8 below, which is an intermediate used in the preparation method of the polyethylene derivatives.

[Formula 8]

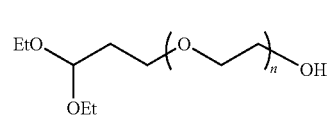

wherein Et is ethyl, and n is directly related to the molecular weight of the polyethylene glycol derivatives to be finally prepared, wherein n may be an integer from 3 to 2000, preferably 7 to 1000 or 10 to 1000, specifically 50 to 500, more specifically 100 to 500, even more specifically 150 to 250, or an integer from 225±25, but is not limited to these.

According to embodiments of the invention, n in the compound of Formula 3 may be 150 to 250.

The present invention provides a compound of Formula 9 below, which is an intermediate used in the preparation method of the polyethylene derivatives.

[Formula 9]

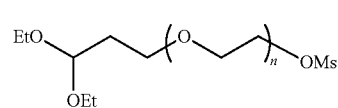

wherein Et is ethyl, Ms is methanesulfonyl, and n is directly related to the molecular weight of the polyethylene glycol derivatives to be finally prepared, wherein n may be an integer from 3 to 2000, preferably 7 to 1000 or 10 to 1000, specifically 50 to 500, more specifically 100 to 500, even more specifically 150 to 250, or an integer from 225±25, but is not limited to these.

According to embodiments of the invention, n in the compound of Formula 9 may be 150 to 250.

In addition, the present invention provides a compound of Formula 10 below, which is an intermediate used in the preparation method of the polyethylene derivatives.

[Formula 10]

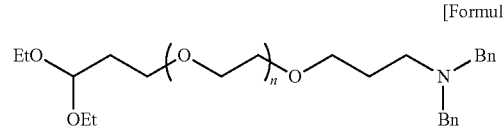

wherein Et is ethyl, Bn is benzyl, and n is directly related to the molecular weight of the polyethylene glycol derivatives to be finally prepared, wherein n may be an integer from 3 to 2000, preferably 7 to 1000 or 10 to 1000, specifically 50 to 500, more specifically 100 to 500, even more specifically 150 to 250, or an integer from 225±25, but is not limited to these.

According to embodiments of the invention, n in the compound of Formula 10 may be 150 to 250.

By using the intermediates of Formulas 2, 3, 4 or 6, the preparation method of the present invention can easily produce a compound of Formula 7 having a high molecular weight, can produce the compound of Formula 7 in high purity and yield, especially under a mild condition, and can also mass-produce the compound of Formula 7 due to the easy purification process.

According to one embodiment of the invention, $R_1$ and $R_2$ in the compounds of Formula 2, Formula 3, Formula 4, Formula 6, and Formula 7 are each independently methyl, ethyl, propyl, isopropyl, butyl, isobutyl, hexyl, heptyl, octyl, or nonyl, and preferably, may be a ($C_1$-$C_4$) alkyl group, and more specifically methyl, ethyl, propyl, isopropyl or butyl. For example, $R_1$ and $R_2$ may be ethyl.

Hereinafter, the present invention will be described with reference to preferred examples. However, the following examples are merely to illustrate the invention. It will be apparent to those skilled in the art that various modifications and variations are possible within the scope and spirit of the invention.

The reagents and solvents mentioned below were purchased from Sigma-Aldrich company, unless otherwise noted, and the purity of the product was measured using HPLC (1200 series, Agilent), and the structure was confirmed using a $^1$H-NMR apparatus.

The compounds 2 to 7 were prepared according to the following Reaction Scheme 6.

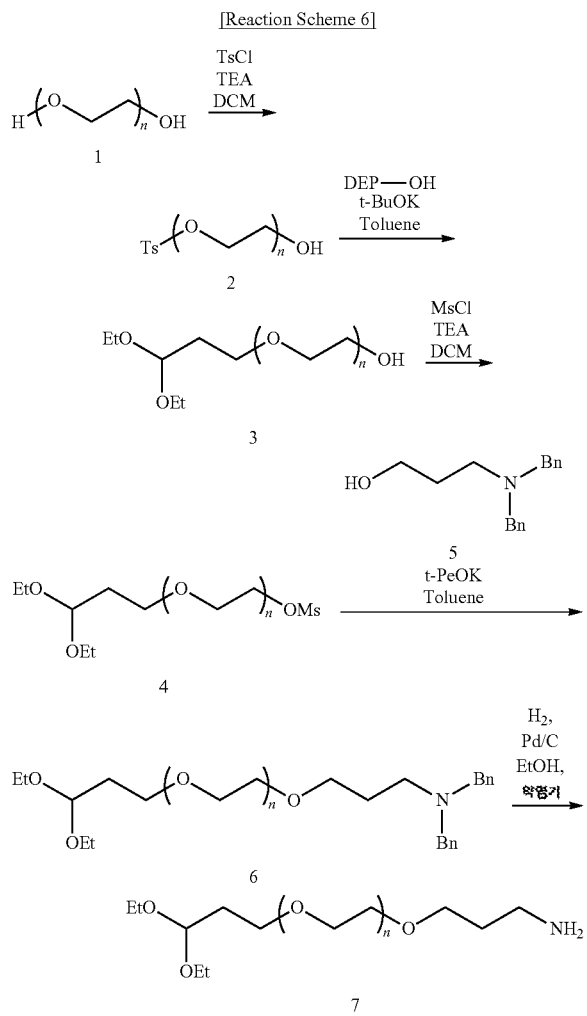

Example 1: Preparation of Compound 2

1 kg of PEG (polyethylene glycol) 10 kDa (1, n=225, manufacturer: Clariant company) and 4 L of dichloromethane were added to the reaction vessel. 112 ㎖ of triethylamine and 153 g of p-toluenesulfonyl chloride were added and stirred at room temperature for 4 hours. After the reaction was completed, water was added and stirred for 5 minutes. After separation of the layers, the extract was washed several times with water. The organic layer was separated, dried over magnesium sulfate, and filtered, and the remaining filtrate was concentrated under reduced pressure. 0.5 L of dichloromethane was added to the concentrate to dissolve it, and then 8 L of methyl t-butylether was added dropwise for 20 minutes. The resulting crystals were filtered, washed with methyl t-butyl ether, and dried at room temperature under nitrogen to obtain 300 g (yield: 30%) of the target compound 2.

$^1$H-NMR (CDCl$_3$, 400 MHz) δ 7.80 (d, 2H, J=8.8 Hz), 7.35 (d, 2H, J=8.4 Hz), 4.17-4.15 (m, 2H), 3.86-3.45 (m, 900H), 2.98 (t, 1H, J=6.4 Hz), 2.45 (s, 3H).

Example 2: Preparation of Compound 3

400 ㎖ of toluene and 10.2 g of diethoxy-1-propanol were added to the reaction vessel. After adding 3.9 g of potassium t-butoxide, the temperature was raised to 50° C. and stirred at 50° C. for 1 hour to prepare an activation solution. 100 g of compound 2 and 400 ㎖ of toluene were added to another reaction vessel, and then heated to 40° C. to dissolve compound 2. The mixture was added dropwise at 40° C. for 20 minutes to the activation solution cooled to 40° C. After stirring at 40° C. for 3 hours, extraction was performed by adding water to the reaction solution. After separation of the layers, dichloromethane was added to the aqueous layer and stirred for 5 minutes. The organic layer was separated, dried over magnesium sulfate, and filtered, and the remaining filtrate was concentrated under reduced pressure. 100 ㎖ of dichloromethane was added to the concentrate to dissolve it, and then 1.5 L of methyl t-butyl ether was added dropwise for 20 minutes. The resulting crystals were filtered, washed with methyl t-butyl ether, and dried at room temperature under nitrogen to obtain 60 g (yield: 60%) of the target compound 3.

$^1$H-NMR (CDCl$_3$, 400 MHz) δ 4.64 (t, 1H, J=6.0 Hz), 3.88-3.40 (m, 900H), 2.70 (t, 1H, J=6.4 Hz), 1.94-1.88 (m, 2H), 1.20 (t, 6H, J=6.8 Hz)

Example 3: Preparation of Compound 4

40 g of compound 3 and 120 ㎖ a of dichloromethane were added to the reaction vessel. 3 ㎖ of triethylamine and 1.5 ㎖ of methanesulfonyl chloride were added while maintaining the reaction temperature at 10° C. or less. Stirring was performed at room temperature for 3 hours. After completion of the reaction, water and dichloromethane were added and stirred for 5 minutes. After extracting the organic layer, dichloromethane was added again to the water layer and extracted further. The organic layers were combined, dried over magnesium sulfate, and filtered and the remaining filtrate was concentrated under reduced pressure. 40 ㎖ of dichloromethane was added to the concentrate to dissolve it, and 600 ㎖ of methyl t-butyl ether was added dropwise for 20 minutes. The resulting crystals were filtered, washed with methyl t-butyl ether and dried at room temperature under nitrogen to obtain 38 g (yield: 95%) of the target compound 4.

$^1$H-NMR (CDCl$_3$, 400 MHz) δ 4.65 (t, 1H, J=6.0 Hz), 4.40-4.38 (m, 2H), 3.85-3.40 (m, 900H), 3.08 (s, 3H), 1.93-1.88 (m, 2H), 1.20 (t, 6H, J=7.2 Hz)

Example 4: Preparation of Compound 6

160 ㎖ of toluene and 10 g of compound 5 were added to the reaction vessel. 11 ㎖ of potassium t-pentoxide (25 wt.

% of toluene solution) was added thereto, the temperature was raised to 50° C., and the solution was stirred at 50° C. for 1 hour (activation solution). 40 g of compound 4 and 400 ml of toluene were added to another reaction vessel, and then heated to 30° C. to dissolve compound 4. The activation solution cooled to 30° C. was added dropwise to the mixture at 30° C. for 1 hour. After stirring for 3 hours at 30° C., extraction was performed by adding water to the reaction solution. After separation of the layers, dichloromethane was added to the aqueous layer and stirred for 5 minutes. The organic layer was separated, dried over magnesium sulfate, and filtered, and the remaining filtrate was concentrated under reduced pressure. 40 ml of dichloromethane was added to the concentrate to dissolve it, and 600 ml of methyl t-butyl ether was added dropwise for 20 minutes. The resulting crystals were filtered, washed with methyl t-butyl ether, and then dried at room temperature under nitrogen to obtain 14 g (yield: 35%) of the target compound 6.

$^1$H-NMR (CDCl$_3$, 400 MHz) δ 7.35-7.18 (m, 10H), 4.63 (t, 1H, J=5.2 Hz), 3.83-3.40 (m, 900H), 2.47 (t, 2H, J=6.8 Hz), 1.92-1.88 (m, 2H), 1.81-1.75 (m, 2H), 1.19 (t, 6H, J=7.2 Hz)

Example 5: Preparation of Compound 7

Example 5-1: Debenzylation with Ammonia 1 g of compound 6 (DEP-PEG-N(Bn)$_2$ (MW=about 10000) n=225), 20 mL of ethanol, and 2 mL of a 28% (v/v) aqueous solution of ammonia were added to the reaction vessel. After dissolution, 0.1 g of Pd/C was added, followed by stirring at room temperature under hydrogen gas for 18 hours. 20 mL of dichloromethane was added dropwise to the reaction solution, stirred for 5 minutes, and filtered to remove Pd/C. The filtrate was distilled under reduced pressure, 1 mL of dichloromethane was added to the concentrate to dissolve it, and 15 mL of methyl t-butyl ether was added dropwise for 20 minutes. The resulting crystals were filtered, washed with methyl t-butyl ether and dried under nitrogen to obtain 0.89 g (yield: 89%) of the target compound 7 (DEP-PEG-NH$_2$ (MW=10000)), which was confirmed by NMR.

$^1$H NMR (CDCl$_3$, 400 MHz) δ 4.64 (t, 1H), 3.85-3.43 (m, 912H), 2.82 (t, 2H), 1.89 (m, 2H), 1.75 (m, 2H), 1.20 (t, 6H).

Example 5-2: Debenzylation with Methylamine 1 g of compound 6 (DEP-PEG-N(Bn)$_2$ (MW=about 10000)), 20 mL of ethanol, and 2 mL of an 40% (v/v) aqueous solution of methylamine were added to the reaction vessel. After dissolution, 0.1 g of Pd/C was added, followed by stirring at room temperature under hydrogen gas for 18 hours. 20 mL of dichloromethane was added dropwise to the reaction solution, stirred for 5 minutes, and filtered to remove Pd/C. The filtrate was distilled under reduced pressure, 1 mL of dichloromethane was added to the concentrate to dissolve it, and 15 mL of methyl t-butyl ether was added dropwise for 20 minutes. The resulting crystals were filtered, washed with methyl t-butyl ether and dried under nitrogen to obtain 0.87 g (yield: 87%) of the target compound 7 (DEP-PEG-NH$_2$ (MW=10000)), which was confirmed by NMR.

$^1$H NMR (CDCl$_3$, 400 MHz) δ 4.62 (t, 1H), 3.42-3.78 (m, 912H), 2.91 (t, 2H), 1.89 (m, 2H), 1.78 (m, 2H), 1.18 (t, 6H).

Example 5-3: Debenzylation with Dimethylamine 0.87 g (yield: 87%) of the target compound 7 (DEP-PEG-NH$_2$ (MW=10000)) was obtained in the same manner as in Example 5-2, which was confirmed by NMR, except that a 50% (v/v) solution of dimethylamine is used instead of aqueous methylamine solution.

$^1$H NMR (CDCl$_3$, 400 MHz) δ 4.63 (t, 1H), 3.42-3.78 (m, 912H), 3.17 (t, 2H), 2.04 (m, 2H), 1.87 (m, 2H), 1.19 (t, 6H).

Comparative Example 1: Debenzylation without Addition of Amine Compound 1 g of compound 6 (DEP-PEG-N(Bn)$_2$ (MW=about 10000)), 20 mL of ethanol, and 2 mL of water were added to the reaction vessel. After dissolution, 0.1 g of Pd/C was added, followed by stirring at room temperature under hydrogen gas for 18 hours. 20 mL of dichloromethane was added dropwise to the reaction solution, stirred for 5 minutes, and filtered to remove Pd/C. The filtrate was distilled under reduced pressure, 1 mL of dichloromethane was added to the concentrate to dissolve it, and 15 mL of methyl t-butyl ether was added dropwise for 20 minutes. The resulting crystals were filtered, washed with methyl t-butyl ether, and dried under nitrogen to obtain 0.9 g of an unknown product. As a result of NMR analysis, it was confirmed that it was not the target compound 6 DEP-PEG-NH$_2$.

Comparative Example 2: Debenzylation with Trimethylamine 1 g of compound 6 (DEP-PEG-N(Bn)$_2$ (MW=about 10000)), 20 mL of ethanol, and 2 mL of an 30% (v/v) aqueous solution of triethylamine were added to the reaction vessel. After dissolution, 0.1 g of Pd/C was added, followed by stirring at room temperature under hydrogen gas for 18 hours. 20 mL of dichloromethane was added dropwise to the reaction solution, stirred for 5 minutes, and filtered to remove Pd/C. The filtrate was distilled under reduced pressure, 1 mL of dichloromethane was added to the concentrate to dissolve it, and 15 mL of methyl t-butyl ether was added dropwise for 20 minutes. The resulting crystals were filtered, washed with methyl t-butyl ether, and dried under nitrogen to obtain 0.88 g of an unknown product. As a result of NMR analysis, it was confirmed that it was not the target compound 6 DEP-PEG-NH$_2$.

TABLE 1

| Item | Example 5-1 | Example 5-2 | Example 5-3 | Comparative Example 1 | Comparative Example 2 |
| --- | --- | --- | --- | --- | --- |
| Amine | ammonia | methylamine | dimethylamine | not used | trimethylamine |
| Target compound | obtained | obtained | obtained | not obtained | not obtained |
| Confirmation of the production of the target compound (NMR) | confirmed (NMR) | confirmed | confirmed | not confirmed | not confirmed |

The invention claimed is:
1. A compound of Formula 10 below:
[Formula 10]
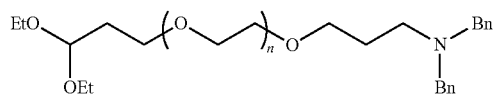
wherein Et is ethyl, Bn is benzyl, and n is an integer from 3 to 2000.
2. The compound according to claim 1, wherein n is an integer from 50 to 500.
3. The compound according to claim 2, wherein n is an integer from 100 to 500.
4. The compound according to claim 3, wherein n is an integer from 150 to 250.
* * * * *